United States Patent
Hisamatsu et al.

(10) Patent No.: US 6,533,754 B1
(45) Date of Patent: Mar. 18, 2003

(54) CATHETER

(75) Inventors: Takatomo Hisamatsu, Fujinomiya (JP); Toshinobu Ishida, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 176 days.

(21) Appl. No.: 09/717,071

(22) Filed: Nov. 22, 2000

(30) Foreign Application Priority Data

Nov. 26, 1999 (JP) .......................................... 11-336082
Jun. 15, 2000 (JP) ...................................... 2000-180450

(51) Int. Cl.⁷ ............................................. A61M 37/00
(52) U.S. Cl. ..................... 604/96.01; 604/535; 606/194
(58) Field of Search ........................... 604/96.01, 535; 606/192, 194

(56) References Cited

U.S. PATENT DOCUMENTS

| | | |
|---|---|---|
| 5,605,543 A | 2/1997 | Swanson |
| 6,102,890 A * | 8/2000 | Stivland et al. .......... 604/96.01 |
| 6,117,106 A * | 9/2000 | Wasicek et al. .......... 604/96.01 |

FOREIGN PATENT DOCUMENTS

| | | |
|---|---|---|
| EP | 0 608 853 A2 | 8/1994 |
| EP | 0 718 003 A1 | 6/1996 |
| EP | 0 925 801 A1 | 6/1999 |
| EP | 0 925 801 | 6/1999 |
| JP | 9-192235 | 7/1997 |

* cited by examiner

*Primary Examiner*—Ronald Capossela
(74) *Attorney, Agent, or Firm*—Burns, Doane, Swecker & Mathis, LLP

(57) ABSTRACT

A dilatation catheter has a tubular proximal shaft having relatively high rigidity, a tubular distal shaft having rigidity lower than that of the proximal shaft, a tubular intermediate section interposed between the proximal shaft and the distal shaft, a hub mounted on the proximal end portion of the proximal shaft, a balloon arranged on the distal end portion of the distal shaft so as to be in fluid communication with the distal shaft, and an inner shaft into which a guide wire can be inserted. The distal end portion of the proximal shaft can be inserted into the intermediate section to form an insertion portion having a spiral slit.

16 Claims, 2 Drawing Sheets

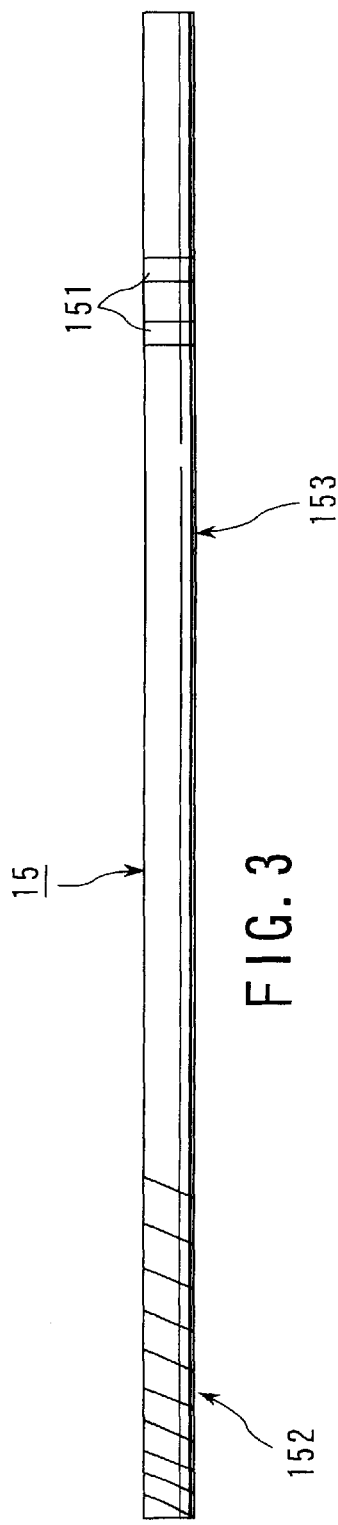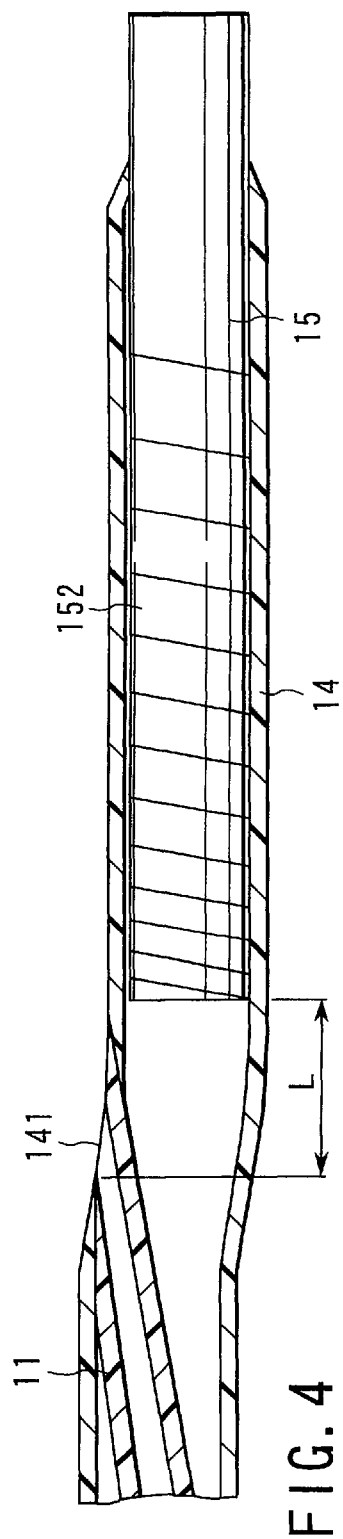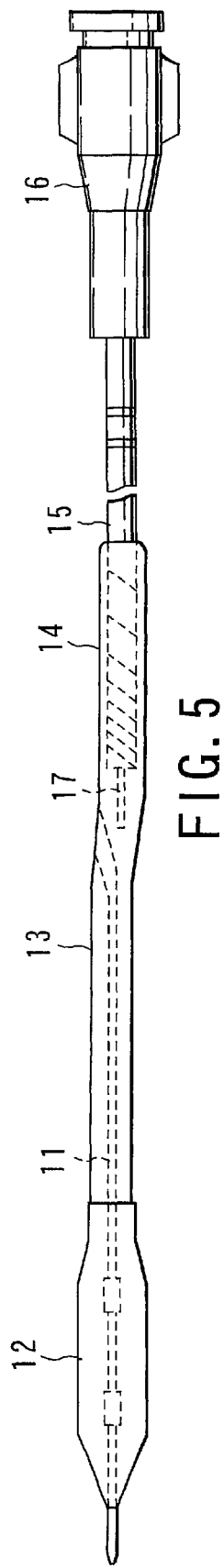

CATHETER

CROSS-REFERENCE TO RELATED APPLICATIONS

This application is based upon and claims the benefit of priority from the prior Japanese Patent Applications No. 11-336082, filed Nov. 26, 1999; and No. 2000-180450, filed Jun. 15, 2000, the entire contents of which are incorporated herein by reference.

BACKGROUND OF THE INVENTION

The present invention relates to a catheter for performing a diagnosis or a treatment of, for example, a blood vessel for carrying out various treatments and to a dilatation catheter for dilating the stenosis within the blood vessel so as to improve the blood flow on the side of the periphery of the stenosis for curing the stenosis.

The advent of a microcatheter has made it possible to perform therapy and diagnosis within a fine blood vessel or vasalium, though the conventional catheter is said to be incapable of performing such a therapy and diagnosis. The microcatheter includes, for example, a percutaneous transluminal coronary angioplasty catheter, hereinafter referred to as a dilatation catheter, used for curing the myocardial infarction or angina pectris. During the angioplasty, it is necessary to exchange the catheter in some cases. For example, it is necessary to exchange the catheter for change of the balloon size, for diagnosis of a region near the stenosis, and for replace of a therapy tool. The method of exchanging the catheter includes a method of using a long exchange guide wire. However, the long exchange guide wire is awkward because it takes time for handling the long wire and at least two operators are required. To overcome this difficulty, used is a "rapid exchange" type catheter. The catheter of this type is constructed such that the distal end portion alone of the catheter tracks the guide wire.

Specifically, a rapid exchange type catheter disclosed in EP 925801A will be described. The catheter is constructed such that a coil assembly comprising a coil and a transition tube covering the coil is provided between a metal tube or a proximal shaft made of a material having a high strength substantially equal to that of the metal tube and a distal shaft made of a resin having a high flexibility so as to moderate a sudden change in rigidity between the proximal shaft of a high strength and the distal shaft of a high flexibility.

In the catheter, however, a clearance is inevitably formed between the proximal shaft and the coil arranged on the distal end side, with the result that the mechanical strength is lowered in the clearance portion, i.e., the portion where the transition tube alone is present. As a result, a problem is generated that the catheter tends to be broken in this portion and the catheter is deteriorated in terms of the pressure resistance. On the other hand, as a method that does not bring about such a clearance portion, it is conceivable to arrange the proximal shaft in a manner to extend into the coil so as to engage the both members, thereby improving the mechanical strength. In this case, however, it is inevitable for the engaged portion between the both members to be enlarged, which is undesirable.

BRIEF SUMMARY OF THE INVENTION

An object of the present invention is provide a rapid exchange type catheter, which permits moderating a sudden change in rigidity between the proximal shaft having a high rigidity and the distal shaft having a flexibility, which is unlikely to be broken over the entire length, and which is excellent in pressure resistance.

According to a first aspect of the present invention, there is provided a dilatation catheter, comprising a tubular proximal shaft having relatively high rigidity; a tubular distal shaft having rigidity lower than that of the proximal shaft; a tubular intermediate section interposed between the proximal shaft and the distal shaft for connecting liquid tightly these shafts; a hub mounted on a proximal end portion of the proximal shaft, to which a pressure applying apparatus can be attached; a balloon arranged to a distal end portion of the distal shaft so as to be in fluid communication with the distal shaft, to which pressure can be applied from the hub; and a guide wire lumen having a distal aperture positioned on a distal end side to the distal end of the balloon and a proximal aperture positioned on a proximal end side to the proximal end of the balloon and on a distal end side to the proximal shaft, wherein a distal end portion of the proximal shaft is inserted into the intermediate section to form an insertion portion, the insertion portion having a spiral slit.

According to a second aspect of the present invention, there is provided a catheter, comprising a tubular proximal shaft having relatively high rigidity; a tubular distal shaft having rigidity lower than that of the proximal shaft; a tubular intermediate section interposed between the proximal shaft and the distal shaft for connecting liquid tightly these shafts; a hub mounted on a proximal end portion of the proximal shaft; a treatment device (device for therapy or diagnose, such as an ultrasonic diagnostic device, a laser, an atherectomy cutter, a medicine supply device, a radio frequency generator or an ultrasonic therapy device) arranged to a distal end portion of the distal shaft; and a guide wire lumen having a distal aperture positioned on a distal end side to the treatment device and a proximal aperture positioned on a proximal end side to the treatment device and on a distal end side to the proximal shaft, wherein a distal end portion of the proximal shaft is inserted into the intermediate section to form an insertion portion, the insertion portion having a spiral slit.

In the present invention, a spiral slit is formed on the proximal shaft, and the distal end portion of the proximal shaft is inserted into the intermediate section to form an insertion portion. As a result, it is possible to change gradually the rigidity of the catheter along the longitudinal direction of the catheter over the proximal shaft, the intermediate section, and the distal shaft.

According to the present invention, it is possible to arrange a reinforcing member on the distal end side relatively to the distal end of the proximal shaft in a manner to extend to reach at least the proximal aperture of the guide wire lumen.

In the present invention, in order to permit the rigidity of the shaft to be changed gradually, it is desirable to form the proximal aperture of the guide wire lumen in the intermediate section and to make the insertion portion of the proximal shaft extend to a region in the vicinity of the proximal aperture of the guide wire lumen.

To be more specific, it is desirable for the distance between the proximal aperture of the guide wire lumen and the distal end of the proximal shaft to be at most 5 mm. Further, in view of the case where the proximal aperture extends over a predetermined length along the longitudinal direction of the catheter, it is desirable for the distance between the distal end of the proximal aperture and the distal end of the proximal shaft to be at most 5 mm.

If the distance between the distal end of the proximal shaft and the proximal aperture of the guide wire lumen, preferably the distance between the distal end of the proximal shaft and the distal end of the proximal aperture of the guide wire lumen having a predetermined length, is set to fall within a range of between 0 and 5 mm, the catheter can exhibit a sufficient mechanical strength and a sufficient pressure resistance in the portion corresponding to the proximal aperture or the portion between the proximal aperture and the distal end of the proximal shaft even if a reinforcing member is not arranged in any of these portions. It follows that it is possible to prevent effectively the kink generation during the operation of the catheter.

In the present invention, it is desirable for the distal end of the spiral slit to be positioned on a portion within 10 mm from the distal end of the proximal shaft toward the proximal end.

In the present invention, it is desirable for the proximal shaft having relatively high rigidity to be formed of a metal tube. For applying a spiral slit processing to the distal end portion of the proximal shaft, it is possible to employ a general technique including, for example, a laser (e.g., YAG laser) processing, a discharge processing, a chemical etching or a cutting process. It is possible to make the pitch of the spiral slit shorter on the distal end side and longer on the proximal end side so as to permit the rigidity of the resultant insertion portion of the proximal shaft to be changed moderately from the proximal end side to the distal end side.

In the catheter of the present invention, it suffices to apply a spiral slit processing to the distal end portion of the proximal shaft. Therefore, it is possible to assemble the catheter without complicated steps. In addition, the insertion portion of the proximal shaft effectively prevents the kink generation. Also, the pitch of the spiral slit is made shorter on the distal end side and longer on the proximal end side so as to permit the rigidity of the insertion portion of the proximal shaft to be changed moderately from the proximal end side to the distal end side. It follows that the kink generation can be prevented more effectively.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 is a view of showing the proximal shaft of the dilatation catheter shown in FIG. 1;

FIG. 4 is a cross sectional view showing the intermediate section, the distal end portion of the proximal shaft and the proximal end portion of the distal shaft; and FIG. 5 is a magnified view of the major members of a dilatation catheter according to another embodiment of the present invention.

DETAILED DESCRIPTION OF THE INVENTION

A dilatation catheter according to the present invention will now be described with reference to the accompanying drawings.

Figure 1:
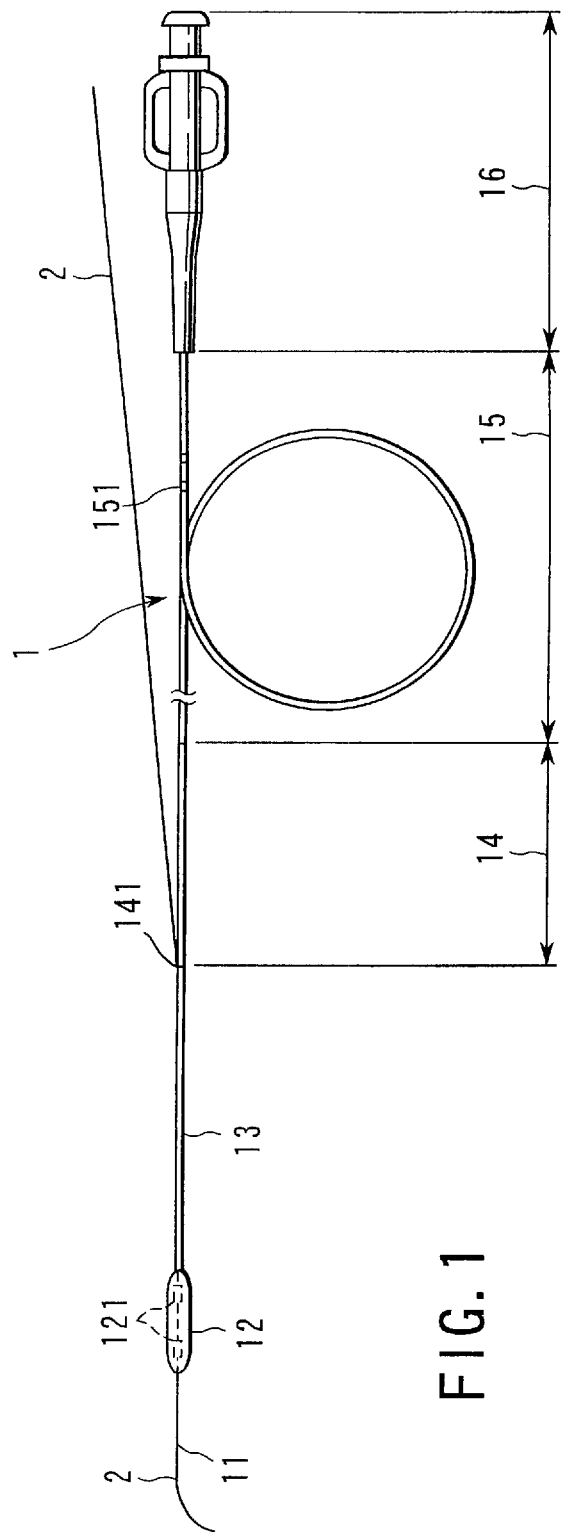
FIG. 1 is a view of a dilatation catheter according to an embodiment of the present invention.
Figure 2:
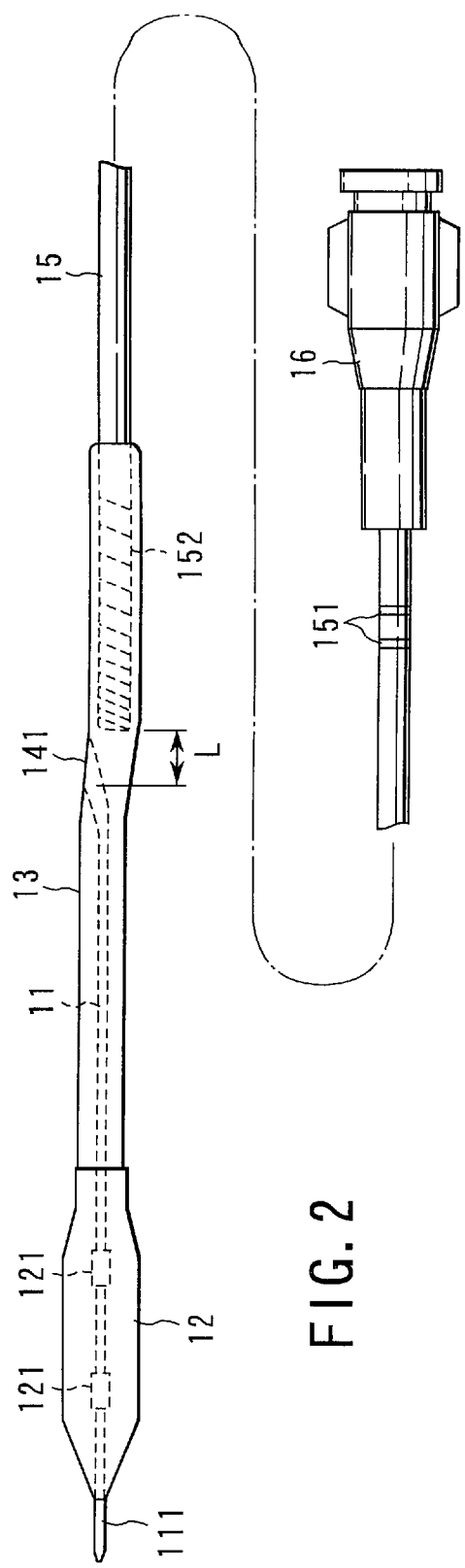
FIG. 2 is a magnified view of the major members of the dilatation catheter shown in FIG. 1.

FIG. 1 shows the appearance of a dilatation catheter 1 according to an embodiment of the present invention. FIG. 2 shows in a magnified fashion the major members of the dilatation catheter shown in FIG. 1, in which the proximal shaft being partly omitted. FIG. 3 shows the appearance of the proximal shaft. Further, FIG. 4 is a cross sectional view showing the intermediate section, the distal end portion of the proximal shaft and the proximal end portion of the distal shaft.

As shown in FIGS. 1 and 2, the dilatation catheter 1 is a so-called rapid exchange type catheter, which is inserted into a blood vessel along a guide wire 2. The dilatation catheter 1 comprises a hub 16, a proximal shaft 15, an intermediate section 14, a distal shaft 13, a balloon 12, and an inner tube shaft 11 arranged in this order as viewed from the proximal end.

A lure taper is formed on the hub 16 of the proximal end side such that a pressure applying apparatus such as an inflator can be attached to the hub 16. The proximal shaft 15 made of a metal or a type of resin having relatively high rigidity is connected to the hub 16 so as to be in fluid communication with the hub 16. The proximal shaft 15 is provided with a depth marker 151, with which it can be easily detected how deep the balloon catheter 1 is inserted along a guiding catheter (not shown) during angioplasty. As described hereinafter in detail, the distal end portion of the proximal shaft 15 constitutes an insertion portion 152.

The intermediate section 14 is connected to the proximal shaft 15 on the distal end side so as to be in fluid communication with the proximal shaft 15. Also, the distal shaft 13 made of a material having relatively low rigidity such as resin is connected to the intermediate section 14 on the distal end side so as to be in fluid communication with the intermediate section 14. Further, the proximal end portion of the balloon 12 is connected to the distal shaft 13 on the distal end side so as to be in fluid communication with the distal shaft 13.

An inner shaft 11 coaxially extends through the inside of the distal shaft 13 and the balloon 12. The distal end portion of the inner shaft 11 forms a distal end tip 111 that extends from the distal end of the balloon 12. The distal end tip 111 is connected liquid tightly to the balloon 12 on the distal end side. On the other hand, the proximal end portion of the inner shaft 11 extends to reach a guide wire aperture 141 formed in a portion from the intermediate section 14 to the distal shaft 13 and is bonded liquid tightly. The inner lumen of the inner shaft 11 extending from the distal end to reach the guide wire aperture 141 forms a guide wire lumen. The guide wire 2 shown in FIG. 1 is inserted through the inner shaft 11 from the distal end aperture of the distal end tip 111 serving as an inlet to the guide wire aperture 141 serving as an outlet. Radiopaque markers 121 are provided around the inner shaft 11 positioned inside the balloon 12.

When the balloon 12 is not inflated, the balloon 12 is folded around the outer circumference of the inner shaft 11. When the balloon 12 is inflated, the balloon 12 is formed such that the center portion becomes substantially cylindrical so as to dilate stenosis of a blood vessel easily. Incidentally, the central portion of the balloon 12 need not be made completely cylindrical. It is possible for the central portion of the balloon 12 to be made polygonal column. The radiopaque markers 121 are provided to facilitate the positioning of the balloon 12 at the stenosis under fluoroscopy during angioplasty.

In the dilatation catheter 1 having the aforementioned structure, when pressure is applied with a pressure applying apparatus (not shown) attached to the hub 16, a pressure medium is transmitted from the hub 16 through the proximal shaft 15, insertion portion of the proximal shaft 152, the intermediate section 14 and the clearance between the distal shaft 13 and the inner shaft 11 so as to reach the balloon 12, and thus the balloon 12 can be inflated. Needless to say, the proximal shaft 15, the intermediate section 14, the distal shaft 13, the inner shaft 11 and each of the bonded portions have resistance to pressure higher than the pressure at which the balloon 12 is ruptured.

FIG. 3 shows in detail the structure of the proximal shaft 15. As shown in the drawing, the proximal shaft 15 comprises a main shaft portion 153 and an insertion portion 152 prepared by applying a spiral slit processing to the distal end portion of the main shaft portion 153. In the drawing, the pitch of the spiral slit is shorter on the distal end side and is longer on the proximal end side. In other words, the pitch is gradually shortened toward the distal end. The insertion portion 152 is formed by applying a laser processing to the distal end portion of the main shaft portion 153. Incidentally, in the present invention, it is possible to decrease the pitch at a predetermined rate from the proximal end portion toward the distal end portion in addition to the construction shown in the drawing.

FIG. 4 shows the structure of the intermediate section 14, the distal end portion of the proximal shaft 15 and the proximal end portion of the distal shaft 13. As shown in the drawing, the insertion portion 152 on the distal end portion of the proximal shaft 15 is inserted into the intermediate section 14. Also, the proximal end portion of the inner shaft 11 is bonded to a part in the outer circumference of the intermediate section 14, and the proximal aperture of the inner shaft 11 is exposed to the outside of the intermediate section 14 so as to form the guide wire aperture 141. Incidentally, it is possible to form the guide wire aperture 141 in the distal shaft 13 or in the boundary region (bonded region) between the intermediate section 14 and the distal shaft 13.

Since the insertion portion 152 is arranged inside the intermediate section 14, it is possible to make the intermediate section 14 lower in rigidity (softer) than the main shaft portion 153 and higher in rigidity (harder) than the distal shaft 13. In this manner, the rigidity of the shaft constituting the dilatation catheter 1 can be gradually changed from the proximal end portion toward the distal end portion. As a result, the stress is not concentrated on a single point when the intermediate section 14 is sharply bent, making it possible to suppress the kink generation.

As described above, in the present invention, a spiral slit process is applied to the distal end portion of the proximal shaft 15 (main shaft portion 153) of the dilatation catheter 1 using a technology that is generally employed such as a laser processing so as to form the insertion portion 152 serving to prevent the kink generation. Since such a simple process can form the insertion portion 152 integral with the main shaft portion 153, it is possible to simplify the assembling process of the catheter, compared with the prior art. Also, since the insertion portion 152 is arranged inside the intermediate section 14, the stress is prevented from being concentrated on a single point when the intermediate section 14 is sharply bent, making it possible to suppress effectively the kink generation. Further, since the pitch of the spiral slit is made smaller on the distal end side and larger on the proximal end side, the rigidity of the entire shaft is changed moderately, making it possible to suppress more effectively the kink generation.

In the present invention, it is desirable for a distance L between the guide wire aperture 141 and the distal end of the proximal shaft 15 to be 5 mm or less. Where the guide wire aperture 141 extends over a predetermined length along the longitudinal direction of the catheter 1 as shown in FIG. 4, the distance L noted above represents the distance between the distal end of the proximal shaft 15 and the distal end of the guide wire aperture 141. If the distance L is short as in the present invention, it is possible to maintain a sufficiently high mechanical strength and pressure resistance of the catheter 1 in the portion corresponding to the guide wire aperture 141 or the portion between the guide wire aperture 141 and the distal end of the proximal shaft 15 even if another reinforcing member is not arranged in any of these portions. As a result, it is possible to prevent effectively the kink generation during the operation of the catheter 1. The present inventors have found that, where the distance L noted above is set at 10 mm, kink is generated during the operation of the catheter 1 with a very high probability in the portion between the guide wire aperture 141 and the distal end of the proximal shaft 15.

Incidentally, it is possible to allow the guide wire aperture 141 not to extend substantially along the longitudinal direction by arranging, for example, the proximal aperture of the inner shaft 11 along the direction perpendicular to the longitudinal axis of the catheter 1. However, where the guide wire aperture 141 is allowed to extend by a predetermined length along the longitudinal direction of the catheter 1 as shown in the drawing, it is possible to decrease the cross sectional area in a direction perpendicular to the longitudinal axis of the catheter 1 at the guide wire aperture 141. As a result, it is possible to ensure a sufficiently large space for permitting the guide wire to be smoothly inserted into and withdrawn through the guide wire aperture 141.

The materials, sizes, etc., of each of the constituents of the dilatation catheter of the present invention will now be described in detail.

It is desirable for the proximal shaft 15 to be made of a material having relatively high rigidity such as a Ni—Ti alloy, brass, SUS, or aluminum. It is also possible to use a resin having relatively high rigidity such as polyimide, polyvinyl chloride, or polycarbonate for forming the proximal shaft 15.

It is desirable for the main shaft portion 153 of the proximal shaft 15 to be formed of a tube having an outer diameter of 0.3 to 3 mm, preferably 0.5 to 1.5 mm, a wall thickness of 10 to 150 $\mu$m, preferably 20 to 100 $\mu$m, and a length of 300 to 2000 mm, preferably 700 to 1500 mm.

It is desirable for the insertion portion 152 of the proximal shaft 15 to be formed of a tube having an outer diameter of 0.3 to 3 mm, preferably 0.5 to 1.5 mm, a wall thickness of 10 to 150 $\mu$m, preferably 20 to 100 $\mu$m, and a length of 30 to 200 mm, preferably 50 to 180 mm.

It is possible for the distal shaft 13 and the intermediate section 14 to be formed of the same tube. Alternatively, it is possible to prepare separately the tube for the distal shaft and the tube for the intermediate section, and to join these two tubes appropriately. Further, the intermediate section 14 may be covered with another tube in order to improve the strength or pressure resistance in the portion between the guide wire aperture 141 and the distal end of the proximal shaft 15.

Where the pitch of the spiral slit in the insertion portion is shorter on the distal end side and longer on the proximal end side as shown in the drawings, the pitch should be 0.1 to 10 mm, preferably 0.3 to 2 mm on the distal end side, and should be 1 to 20 mm, preferably 2 to 10 mm on the proximal end side. Also, the width of the spiral slit should be not larger than 1 mm, preferably about 0.01 to 0.5 mm. It is desirable for the distal end of the spiral slit to be positioned on a portion within 10 mm from the distal end of the proximal shaft 15 toward the proximal end. It is more desirable for the distal end of the slit to extend to reach the distal end of the proximal shaft 15. Where the spiral slit is formed to reach a region in the vicinity of the distal end of the proximal shaft 15, the distal end portion of the proximal shaft 14 can be bent satisfactorily in the case of sharply bending the intermediate section 14, making it possible to prevent the stress from being concentrated on a single point. As a result, the kink generation can be suppressed effectively.

The distal shaft 13 and the intermediate section 14 can be formed of polymer materials including, for example, polyolefin such as polyethylene, polypropylene, polybutene, ethylene-propylene copolymer, ethylene-vinyl acetate copolymer, ionomer, and a mixture of at least two of them, cross-linked polyolefin, polyvinyl chloride, polyamide, polyamide elastomer, polyester, polyester elastomer, polyurethane, polyurethane elastomer, fluoroplastic, and polyimide and a mixture thereof. Further, the material for the intermediate section 14 should preferably be higher in rigidity than the material for the distal shaft 13.

Each of the distal shaft 13 and the intermediate section 14 is formed of a tube having an outer diameter of 0.5 to 1.5 mm, preferably 0.7 to 1.1 mm, a wall thickness of 25 to 200 $\mu$m, preferably 50 to 100 $\mu$m, and a length of 300 to 2000 mm, preferably 300 to 1500 mm.

The inner tube shaft 11 is formed of a material having flexibility to some extent. For example, the inner tube shaft 11 is formed of polymer materials including, for example, polyolefin such as polyethylene, polypropylene, polybutene, ethylene-propylene copolymer, ethylene-vinyl acetate copolymer, ionomer, or a mixture of at least two of them, cross-linked polyolefin, polyvinyl chloride, polyamide, polyamide elastomer, polyester, polyester elastomer, polyurethane, polyurethane elastomer, polyimide and fluoroplastic and a mixture thereof.

Where the guide wire aperture 141 extends over a predetermined length along the longitudinal direction of the catheter 1 as shown in the drawings, the length of the guide wire aperture 141 in the longitudinal direction of the catheter 1 should be about 0.5 to 8 mm, preferably about 2 to 5 mm.

The inner shaft 11 is formed of a tube having an outer diameter of about 0.1 to 1.0 mm, preferably 0.3 to 0.7 mm, a wall thickness of about 10 to 150 $\mu$m, preferably 20 to 100 $\mu$m, and a length of 100 to 2000 mm, preferably 200 to 1500 mm.

It is desirable to use a material having a flexibility to some extent for forming the balloon 12 in order to enable the balloon 12 to dilate the stenosis of the blood vessel. Specifically, the balloon 12 can be formed of polymer materials including, for example, polyolefin such as polyethylene, polypropylene, polybutene, ethylene-propylene copolymer, ethylene-vinyl acetate copolymer and ionomer, cross-linked polyolefin, polyester such as polyethylene terephthalate, polyester elastomer, polyvinyl chloride, polyurethane, polyurethane elastomer, polyphenylene sulfide, polyamide, polyamide elastomer, and fluoroplastic, as well silicone rubber and latex rubber. It is also possible to use a laminated film prepared by suitably laminating films of these polymer materials. It is possible to bond the balloon 12 prepared by the biaxial orientation blow forming method to the distal end portion of the distal shaft 13. Alternatively, it is possible to apply an orientation blow forming to the distal end portion of the distal shaft 13 for integrally forming the balloon 12.

Where the balloon 12 is inflated, it is desirable for the cylindrical portion of the inflated balloon 12 to have an outer diameter of 1.0 to 10 mm, preferably 1.0 to 5.0 mm, and a length of 5 to 50 mm, preferably 10 to 40 mm. Also, it is desirable for the balloon 12 to have an entire length of 10 to 70 mm, preferably 15 to 60 mm.

It is desirable for the radiopaque markers 121 to be formed of a coil spring or a ring. It is necessary to arrange at least two or more radiopaque markers 121. It is desirable for the radiopaque markers 121 to be made of a material having a high capability of forming an X-ray image including, for example, Pt, Pt alloy, W, W alloy, Au, Au alloy, Ir, Ir alloy, Ag and Ag alloy.

The catheter of the present invention described above is of a coaxial structure in which the guide wire lumen is coaxially arranged within the distal shaft. However, the catheter of the present invention is not limited to the particular construction. It is possible for the catheter to be constructed such that a guide wire lumen and a balloon inflation lumen are arranged in parallel within a single tube (shaft).

FIG. 5 shows a catheter according to another embodiment of the present invention. In this embodiment, a reinforcing wire 17 is arranged for reinforcing the portion between the proximal shaft having high mechanical strength and the proximal aperture of the guide wire lumen. In this embodiment, the proximal end portion of the reinforcing wire 17 is fixed to the inside of the hub 16, and the reinforcing wire 17 extends within the proximal shaft and further extends from the distal end of the proximal shaft to reach a portion corresponding to the guide wire aperture. Incidentally, it is possible for the reinforcing wire 17 to extend further beyond the guide wire aperture toward the distal end. By this construction, a portion that is not supported by either the guide wire inserted into the guide wire lumen or the proximal shaft is reinforced by the reinforcing shaft 17 so as to increase the mechanical strength and the pressure resistance of the particular portion.

In the embodiment shown in FIG. 5, the reinforcing wire 17 extends from within the hub through the inner region of the proximal shaft. However, the present invention is not limited to the particular construction. For example, it is possible to fix the proximal end portion of the wire to the distal end portion of the proximal shaft by welding or with an adhesive.

As described above in detail, the present invention provides a catheter, in which an insertion portion integral with the proximal shaft is formed by applying a spiral slit process to the distal end portion of the proximal shaft by a simple process such as a laser processing so as to prevent the kink occurrence in the portion having low rigidity. Also, if the distance between the distal end of the proximal shaft and the distal end, which is positioned forward of the distal end of the proximal shaft, of the proximal aperture of the guide wire lumen is set at 5 mm or less, the catheter is enabled to exhibit a sufficiently high mechanical strength and a sufficiently high pressure resistance even if a reinforcing member is not arranged in the portion corresponding to the proximal aperture and in the portion between the proximal aperture and the distal end of the proximal shaft, making it possible to prevent effectively the kink occurrence during the operation of the catheter.

Particularly, the pitch of the spiral slit is made shorter on the distal end side and is made longer on the proximal end side in the present invention, making it possible to permit the rigidity to be changed moderately over the entire length of the shaft. It follows that the kink generation can be prevented more effectively.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A dilatation catheter, comprising:
   a tubular proximal shaft;
   a tubular distal shaft having rigidity lower than that of the proximal shaft;
   a tubular intermediate section interposed between the proximal shaft and the distal shaft for connecting liquid tightly these shafts;
   a hub mounted on a proximal end portion of the proximal shaft, to which a pressure applying apparatus can be attached;
   a balloon arranged on a distal end portion of the distal shaft so as to be in fluid communication, to which pressure can be applied from the hub; and
   a guide wire lumen having a distal aperture positioned on a distal end side to the distal end of the balloon and a proximal aperture positioned on a proximal end side to the proximal end of the balloon and on a distal end side to the proximal shaft,
   wherein a distal end portion of the proximal shaft is inserted into the intermediate section to form an insertion portion, the insertion portion having a spiral slit.

2. The dilatation catheter according to claim 1, wherein a distance between the proximal aperture of the guide wire lumen and the distal end of the proximal shaft is at most 5 mm.

3. The dilatation catheter according to claim 1, wherein the proximal aperture of the guide wire lumen extends over a predetermined length in a longitudinal direction of the catheter, and the distance between the distal end of the proximal aperture and the distal end of the proximal shaft is at most 5 mm.

4. The dilatation catheter according to claim 1, wherein the distal end of the spiral slit is positioned on a portion within 10 mm from the distal end of the proximal shaft toward the proximal end.

5. The dilatation catheter according to claim 1, further comprising a reinforcing member arranged on the distal end side to the distal end of the proximal shaft in a manner to extend to reach at least the proximal aperture of the guide wire lumen.

6. The dilatation catheter according to claim 1, wherein the proximal shaft is formed of a metal tube.

7. The dilatation catheter according to claim 1, wherein a pitch of the spiral slit is shorter on the distal end side and longer on the proximal end side.

8. The dilatation catheter according to claim 1, further comprising an inner shaft arranged coaxially, with the distal shaft inside the distal shaft, and the inner lumen of the inner shaft forms the guide wire lumen.

9. A catheter, comprising:
   a tubular proximal shaft;
   a tubular distal shaft having rigidity lower than that of the proximal shaft;
   a tubular intermediate section interposed between the proximal shaft and the distal shaft for connecting liquid tightly these shafts;
   a hub mounted on a proximal end portion of the proximal shaft;
   a treatment device arranged on a distal end portion of the distal shaft; and
   a guide wire lumen having a distal aperture positioned on a distal end side to the treatment device and a proximal aperture positioned on a proximal end side to the treatment device and on a distal end side to the proximal shaft,
   wherein a distal end portion of the proximal shaft is inserted into the intermediate section to form an insertion portion, the insertion portion having a spiral slit.

10. The catheter according to claim 9, wherein a distance between the proximal aperture of the guide wire lumen and the distal end of the proximal shaft is at most 5 mm.

11. The catheter according to claim 9, wherein the proximal aperture of the guide wire lumen extends over a predetermined length in a longitudinal direction of the catheter, and the distance between the distal end of the proximal aperture and the distal end of the proximal shaft is at most 5 mm.

12. The catheter according to claim 9, wherein the distal end of the spiral slit is positioned on a portion within 10 mm from the distal end of the proximal shaft toward the proximal end.

13. The catheter according to claim 9, further comprising a reinforcing member arranged on the distal end side to the distal end of the proximal shaft in a manner to extend to reach at least the proximal aperture of the guide wire lumen.

14. The catheter according to claim 9, wherein the proximal shaft is formed of a metal tube.

15. The catheter according to claim 9, wherein a pitch of the spiral slit is shorter on the distal end side and longer on the proximal end side.

16. The catheter according to claim 9, further comprising an inner shaft arranged coaxially with the distal shaft inside the distal shaft, and the inner lumen of the inner shaft forms the guide wire lumen.

* * * * *